(12) United States Patent
Johnson et al.

(10) Patent No.: US 7,234,468 B2
(45) Date of Patent: Jun. 26, 2007

(54) TRANSVERSE CAVITY DEVICE AND METHOD

(75) Inventors: Wesley Johnson, Eden Prairie, MN (US); Deborah A. Barber, Shakopee, MN (US); Thomas Hektner, Medina, MN (US); Larry Fuller, Woodbury, MN (US); Lawrence Wales, Maplewood, MN (US)

(73) Assignee: Spine Wave, Inc., Shelton, CT (US)

( * ) Notice: Subject to any disclaimer, the term of this patent is extended or adjusted under 35 U.S.C. 154(b) by 79 days.

(21) Appl. No.: 11/073,796

(22) Filed: Mar. 7, 2005

(65) Prior Publication Data

US 2005/0182413 A1    Aug. 18, 2005

Related U.S. Application Data

(63) Continuation of application No. 09/873,699, filed on Jun. 4, 2001, now Pat. No. 7,114,501.

(60) Provisional application No. 60/227,050, filed on Aug. 21, 2000, provisional application No. 60/225,191, filed on Aug. 14, 2000.

(51) Int. Cl.
*A61B 17/00* (2006.01)

(52) U.S. Cl. .................. 128/877; 606/61; 606/79; 606/86

(58) Field of Classification Search ............ 128/887, 128/877; 606/60–61, 79–96
See application file for complete search history.

(56) References Cited

U.S. PATENT DOCUMENTS

| | | |
|---|---|---|
| 3,030,951 A | 4/1962 | Mandarino |
| 4,262,676 A | 4/1981 | Jamshidi |
| 4,542,741 A | 9/1985 | Burgin |
| 4,554,914 A | 11/1985 | Kapp et al. |
| 5,013,318 A | 5/1991 | Spranza, III |
| 5,171,248 A | 12/1992 | Ellis |
| 5,231,169 A * | 7/1993 | Constantz et al. .......... 530/356 |
| 5,403,318 A | 4/1995 | Boehringer |
| 5,415,660 A | 5/1995 | Campbell et al. |
| 5,423,824 A | 6/1995 | Akerfeldt et al. |
| 5,445,639 A | 8/1995 | Kuslich et al. |
| 5,468,245 A | 11/1995 | Vargas, III |
| 5,505,733 A | 4/1996 | Justin et al. |
| 5,505,738 A | 4/1996 | Hempel et al. |
| 5,522,398 A | 6/1996 | Goldenberg et al. |
| 5,591,170 A | 1/1997 | Spievack et al. |
| 5,695,513 A | 12/1997 | Johnson et al. |
| 5,816,257 A * | 10/1998 | Chin .......................... 128/898 |
| 5,827,328 A | 10/1998 | Buttermann |
| 5,928,239 A * | 7/1999 | Mirza .......................... 606/79 |

(Continued)

FOREIGN PATENT DOCUMENTS

WO    WO 97/31577    4/1997

(Continued)

*Primary Examiner*—Michael A. Brown
(74) *Attorney, Agent, or Firm*—Maginot, Moore & Beck (57) ABSTRACT

A method for treating a compression fracture in a bone includes the step of forming a transverse cavity and then applying a force within the cavity generally normal to a surface of the bone to restore it substantially to its normal anatomic shape. In certain embodiments, the force is applied by an expandable device.

26 Claims, 7 Drawing Sheets

U.S. PATENT DOCUMENTS

| | | |
|---|---|---|
| 6,068,642 A | 5/2000 | Johnson et al. |
| 6,119,697 A * | 9/2000 | Engel et al. ................ 128/885 |
| 6,127,597 A | 10/2000 | Beyar et al. |
| 6,383,188 B2 | 5/2002 | Kuslich et al. |
| 6,440,138 B1 | 8/2002 | Reiley et al. |
| 6,575,978 B2 | 6/2003 | Peterson et al. |
| 6,676,665 B2 | 1/2004 | Foley et al. |

FOREIGN PATENT DOCUMENTS

| | | |
|---|---|---|
| WO | WO99/00074 | 1/1999 |
| WO | WO99/252453 | 5/1999 |
| WO | WO99/34737 | 7/1999 |
| WO | WO99/56675 | 11/1999 |

* cited by examiner

TRANSVERSE CAVITY DEVICE AND METHOD

CROSS-REFERENCE TO RELATED CASES

The present application claims the benefit of, and incorporates by reference, application Ser. No. 09/873,699, which was filed on Jun. 4, 2001, now U.S. Pat. No. 7,114,501 and which claims the benefit of, and incorporates herein by reference to, the following US provisional applications:

U.S. Provisional Patent Application Ser. No. 60/227,050 filed Aug. 21, 2000, entitled "Vertebroplasty Cavity Creation using an Expanding Tube" and, U.S. Provisional Patent Application Ser. No. 60/225,191 filed Aug. 14, 2000, entitled "Vertebral Body Expander."

FIELD OF THE INVENTION

The present invention relates generally to the treatment of compression fractures in bones, and more specifically to a device and a method for cutting a "transverse" cavity in the bone as one part of a therapy.

BACKGROUND OF THE INVENTION

The human spine consists of a complex set of interrelated anatomic elements including a set of bones called vertebral bodies. Intervertebral discs separate most vertebral bodies. These discs includes a "spongy" nucleus pulpous surrounded by an annulus fibrosis "membrane." The annulus fibrosis connects the opposed endplates of adjacent vertebral bodies. All of these structures together with muscles act to provide motion, stability and protection for the spinal cord. When healthy, these structures effectively protect the spinal cord and allow for normal motion.

However, there are many disease states and aging processes that impact the patient. Osteoporosis and metastatic disease reduce the structural integrity of the vertebral bodies, predisposing them to fracture. Vertebral fractures can lead to loss of vertebral height, which can exacerbate existing neurological conditions or predispose the spine to other symptoms. Back pain often results from these conditions.

Vertebroplasty is an effort to stabilize these fractures and to alleviate this source of pain. Generally, if not treated, fractures and loss of height result in a cascade of injury which is undesirable. For this reason, various efforts have been directed at stabilizing and restoring the natural vertebral bodies of the back.

Many surgeon experts suggest that it is desirable to intervene and restore the height of the vertebral body and natural biomechanics of the spine, in addition to stabilizing the spine to provide pain relief. As an initial step to fracture reduction, which for vertebral compression fractures restores anatomic vertebral height, it may be desirable to cut a cavity that is approximately transverse to the vertical axis of the vertebral body. This cavity is intended to create a large, uniform, initial surface area for fracture reduction devices. The transverse cavity reduces contact stress in supporting bone and decreases the likelihood of cancellous compaction associated with prior art techniques. Thus, this step increases the likelihood that the fracture will be reduced rather than simply creating a large cavity within a bony structure. In general, it may be desirable to locate this transverse cavity near the fracture, which is generally located in the anterior portion of the vertebral body. It is important to create a shallow cavity at the correct location to minimize disruption of cancellous bone and to facilitate further therapeutic intervention.

The presently available techniques and devices expand along a path of least resistance within the cancellous bone. As a result, these devices do not expand in a predictable manner, often expanding vertically before expanding horizontally (transverse). Rather than consistently reducing the fracture, these techniques often crush the cancellous bone, creating an expanded cavity without necessarily reducing the fracture or restoring the natural anatomy.

Another reason for creating a narrow cavity is to impart known fracture zones in the bone. These fracture zones enable controlled movement of the bone during other therapeutic procedures. These fracture zones also create flow channels for various injectable materials that may be used in a further therapeutic intervention.

SUMMARY

Figure 13:
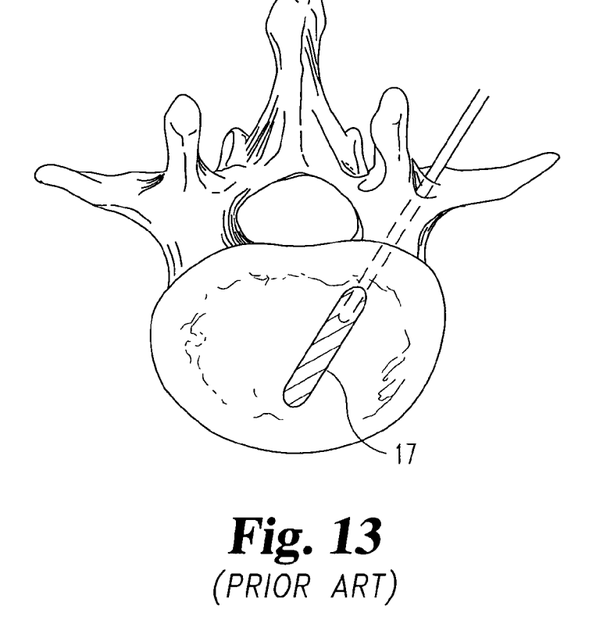
FIG. 13 is a cross section of a vertebral body illustrating a portion of a hydraulic lifting device of the Prior Art; and, FIG. 14 is a cross section of a vertebral body illustrating a portion of a hydraulic lifting device.
Figure 14:
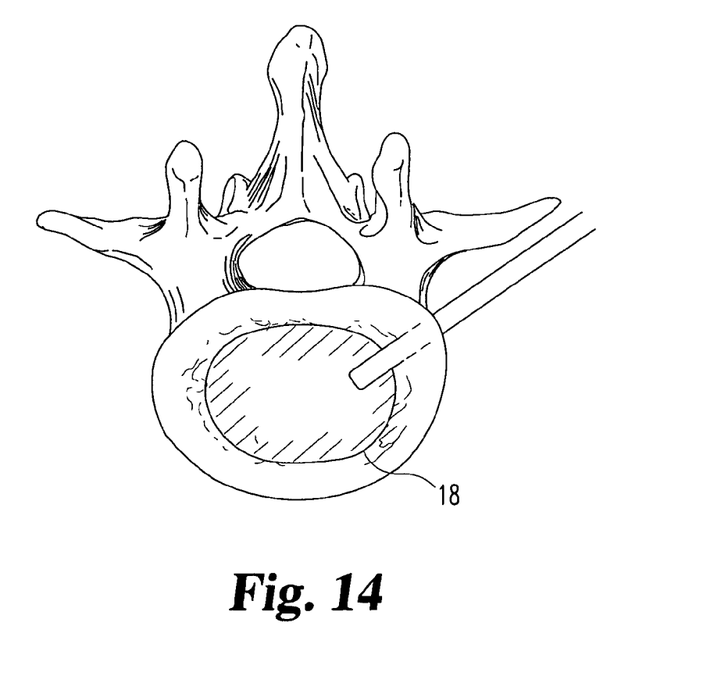

In contrast to the prior art, the devices and methods of the present invention are used to create an initial cavity in the vertebral body that has a controlled shape and location. FIG. 13 represents a prior art procedure where a narrow and small cavity 17 is filled with a balloon and the overall "footprint" is small so that the total distraction force is also small. FIG. 14 represents a cavity created according to the invention filled with a balloon to apply distraction force. In this figure, the increased area of the "footprint" of the transverse cavity 18 permits greater distraction force per unit balloon pressure.

The vertebral body is entered through either a transpedicular or extrapedicular location with a needle, trocar or other access devices. The cavity creation tool of the invention is inserted into the cancellous bone of the vertebral body through the relatively small area aperture created by the trocar or needle. The cavity creation tool is then activated and manipulated.

In general, the tool is directed to a site near the bone fracture. In the context of a vertebral compression fracture, the fracture is typically located in the anterior portion of the vertebral body. Once positioned at the desired site, the device is used to create a cavity. Although several related embodiments of the cavity creation tool are contemplated and illustrated, each of them defines a cutting or shearing plane. Each device limits its action to a controlled area of the bone. The controlled area both defines and is a portion of the "transverse" cavity.

Once the preferred transverse cavity is created, any number of interventions can be performed. For example, a device that "expands" may be introduced to reduce the fracture. Typically, the reduction is intended to restore the normal anatomy. This expansion device may be removed or permanently implanted.

Once a fracture is reduced, the bone cavity may be filled with a bone filler material such as bone cement, allograft, or synthetic bone substitutes. The filler acts to increase the stability and strength of the bone. In some interventions, the filler may be combined with bone growth factors (BMPs, cell therapy, autologous growth factors) to accelerate bone remolding and increase the amount of bone remodeling. Likewise, other drugs or therapies (including but not limited to antibiotics, chemotherapy, and other drug therapies) may be combined with the bone filler.

Although the invention is illustrated within the vertebral body compression fracture treatment context, other secondary interventions or operations can be contemplated for using the shaped cavity.

Although the invention is particularly useful for the treatment of vertebral bodies, it should be understood that similar bone fracture geometries exist in other parts of the body. For this reason, the devices and methods of the invention may be used in the treatment of any compaction fracture, such as but not limited to the tibial plateau fractures, distal radius fractures, calcaneous, distal tibial fractures, and humeral fractures.

BRIEF DESCRIPTION OF THE DRAWINGS

Illustrative embodiments of the inventions are shown throughout the several views of the drawings. For ease of illustration, the inventions are disclosed in the context of the repair of a vertebral body, however the device and method can be applied in other compression fracture applications including, but not limited to tibial plateau, distal radius, calcaneous, distal tibial fractures, and humeral fractures.

In these illustrative but not limiting drawings, like reference numerals indicate equivalent structure, wherein.

DETAILED DESCRIPTION

Figure 1:
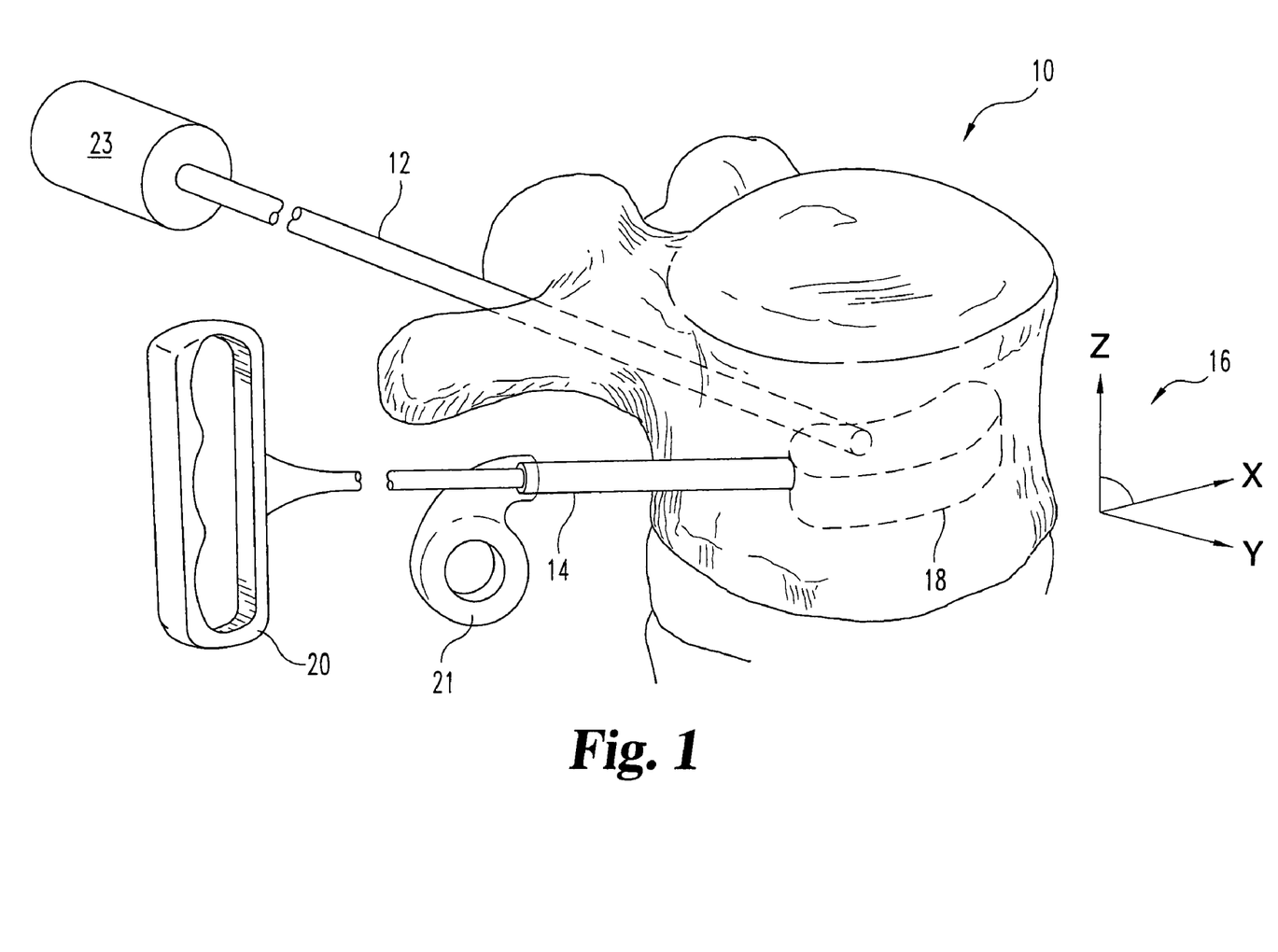
FIG. 1 is a phantom view of a vertebral body showing a transverse cavity, certain tool features and a coordinate system.

FIG. 1 is a phantom view of a vertebral body showing a transverse cavity 18 and a coordinate system 16. This figure shows a vertebral body 10 in isolation. Two possible surgical entry points into the vertebral body contemplated within the scope of the invention are illustrated. One entry point is "transpedicular." This approach is indicated by the physical location of tube 12, traveling through the pedicle into the vertebral body 10. Another approach is "extra-pedicular." This access approach is illustrated by tool 14 entering the vertebral body at a location lateral of the transpedicular approach on the posterolateral corner of the vertebral body.

The typical surgery will include a small incision in the back adjacent to the vertebral body. Next, a small gauge needle or guide-wire is introduced to confirm proper positioning under fluoroscopy. Physicians typically utilize an 11-gauge needle for the transpedicular approach and a larger needle or tube (up to 6 mm ID) for the extra-pedicular approach. Many physicians advance cannulated tools over a small gauge needle to successively increase the size of the working channel.

Other physicians may prefer to place a guide catheter at the site and to introduce tools though the lumen of the guide catheter. In general, the tools described herein can be used either over the wire or through a guide catheter or alone at the election of the physician.

In this figure, a coordinate system 16 identifies a vertical direction Z, which points along the spine. The Y-direction is generally anterior. It is the purpose of the invention to create a cavity with a fixed and controlled vertical extent (Z-axis height) and a controlled shape in the X-Y plane. For the purposes of this disclosure, the term transverse cavity will be used interchangeably with a cavity created parallel to the surface that is to be reduced or restored to its normal anatomic position, and generally normal to the force applied. The surface that is reduced or displaced defines the X-Y plane. This definition holds for other procedures performed with the invention.

Returning to the figure, the cavity 18 is typically ovaloid in shape as projected in the X-Y plane. The ovaloid shape has an approximately uniform height in the Z direction. This "shape" is referred to throughout the specification as a "transverse cavity" for the vertebral body application illustrated in these figures. Therefore the X-Y plane is defined as the "transverse plane" and the Z-axis direction may be referred to as the "vertical axis." It is a characteristic of all the embodiments of the tools shown in the application that the cross sectional area of the tool at the entry point into the bone is smaller than the transverse cavity created with the tool.

To facilitate description of the invention, the distal "working" structures of the cavity creation tools are illustrated in isolation while the proximal manipulation handles as contemplated are shown generically as handle 20 and finger loop 21. In each embodiment, a handle structure 20 can be moved with respect to the tool sheath or tool body 14. In each embodiment, the relative motion between handle 20 and sheath 14 activates the distal working surfaces of the device. The handle 20 or the finger loop 21 is indexed to the distal working surfaces to provide confirmation of the orientation of the working surfaces with respect to the bone structures.

It is contemplated that in addition to direct manual manipulation, other power sources can be used to actuate the working surfaces, including hydraulic or pneumatic cylinders and electromechanical actuators shown generically in FIG. 1 as power source 23. In general, purely manual mechanical mechanisms are preferred because they improve tactile feedback to the physician.

The tools may be made of conventional materials, with stainless steel preferred for "blade" embodiments and Nitinol or other super elastic alloys adopted for the flexible arm embodiments. The tools may be reusable or disposable. Materials choices do not appear critical for carrying out the invention.

The overall length of the cavity creation tool from the handle structures 20 and 21 to the working distal tip may vary to facilitate the particular surgical procedure. For example, a length of 220 cm is useful for the vertebral application, while a length of 60 cm is a practical value for a tibial plateau procedure.

Figure 2:
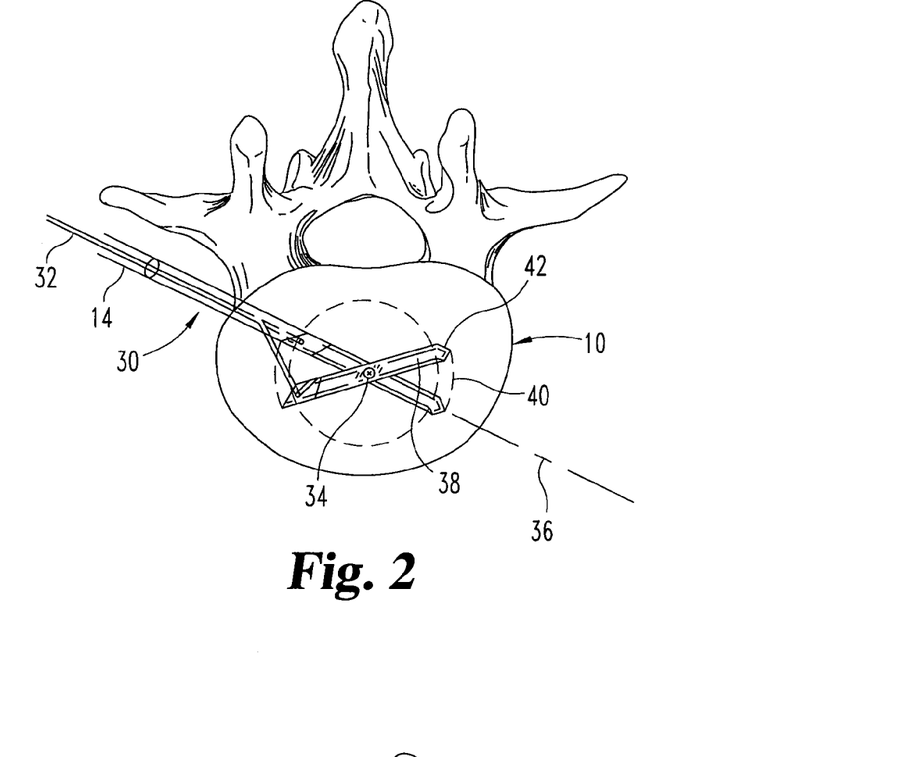
FIG. 2 is a cross section of a vertebral body illustrating a portion of a cavity creation tool.

FIG. 2 shows an embodiment of the cavity creation tool 30 that includes a blade 38 mounted on the tool body 14 for rotational motion around the pivot 34. The rod 32 is coupled to a proximal handle 20 (FIG. 1) and a push-pull motion between the handle and the finger loop 21 (FIG. 1) causes the blade to sweep out an arc 40. The blade may be blunt or it may include a cutting surface 42. In operation, the blade 38 laterally loads cancellous bone, breaking or cutting the bone in the X-Y plane of the cavity. The pivot and blade are confined to a transverse plane so this action creates the transverse cavity. By advancing the tool along the axis 36, the cavity may take an approximately oval shape in the X-Y plane.

Figure 3:
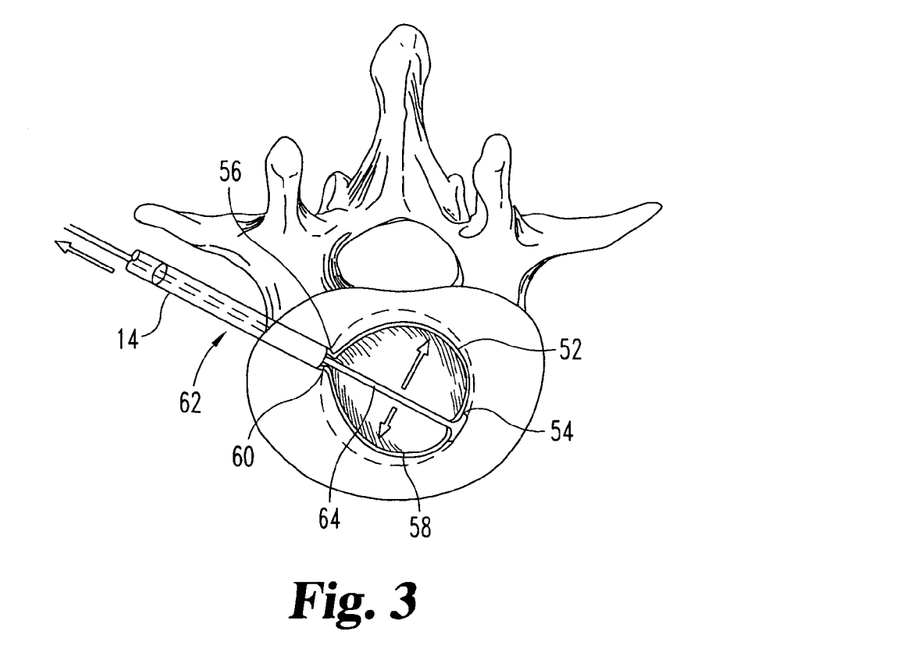
FIG. 3 is a cross section of a vertebral body illustrating a portion of a cavity creation tool.

FIG. 3 shows a cavity creation tool 62 having a distal end that is positioned in a vertebral body. The distal end includes two arms. A first arm 52 is anchored to the tube 14 with a hinge point mechanism 56 at a first end. The second end of the arm 52 is coupled to the pull rod 64. Relative motion between the tube 14 and the pull rod 64 expands the first arm in a transverse plane. This particular embodiment of the tool is asymmetric and the tool includes a second arm 58 that is anchored to the tube 14 with a hinge mechanism 60. The first and second arms define a plane for the operation of the device in the transverse plane.

Figure 4:
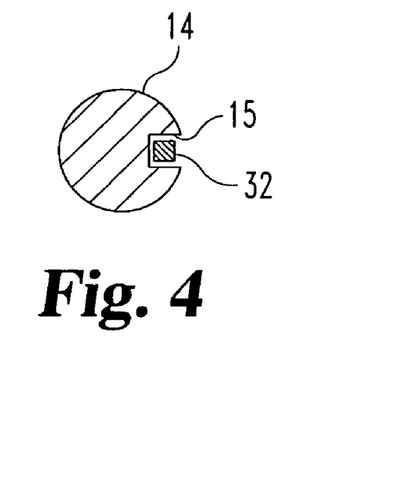
FIG. 4 is a cross section of a portion of a cavity creation tool.

FIG. 4 shows a cross section of the tool body 14 having a notch or groove 15 for locating and restraining a pull rod 32. The tool body cross section defines the tool body area for the cavity creation tool. In general, the tool may be inserted into a bone through a hole of the size of the tool body area. This parameter or area is always smaller than the "footprint" of the transverse cavity in the X-Y plane. The cross section of this portion of the tool defines the tool body area.

Figure 5:
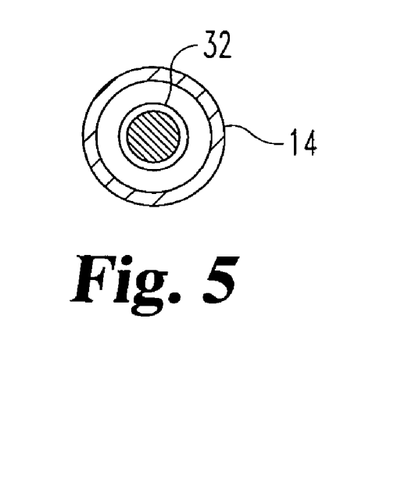
FIG. 5 is a cross section of a portion of a cavity creation tool.

FIG. 5 shows a pull rod 32 is constrained in a groove in the tool body 14. In this embodiment the pull rod actuates a blade or other structure. The cross section of this portion of the tool defines the tool body area.

Figure 6:
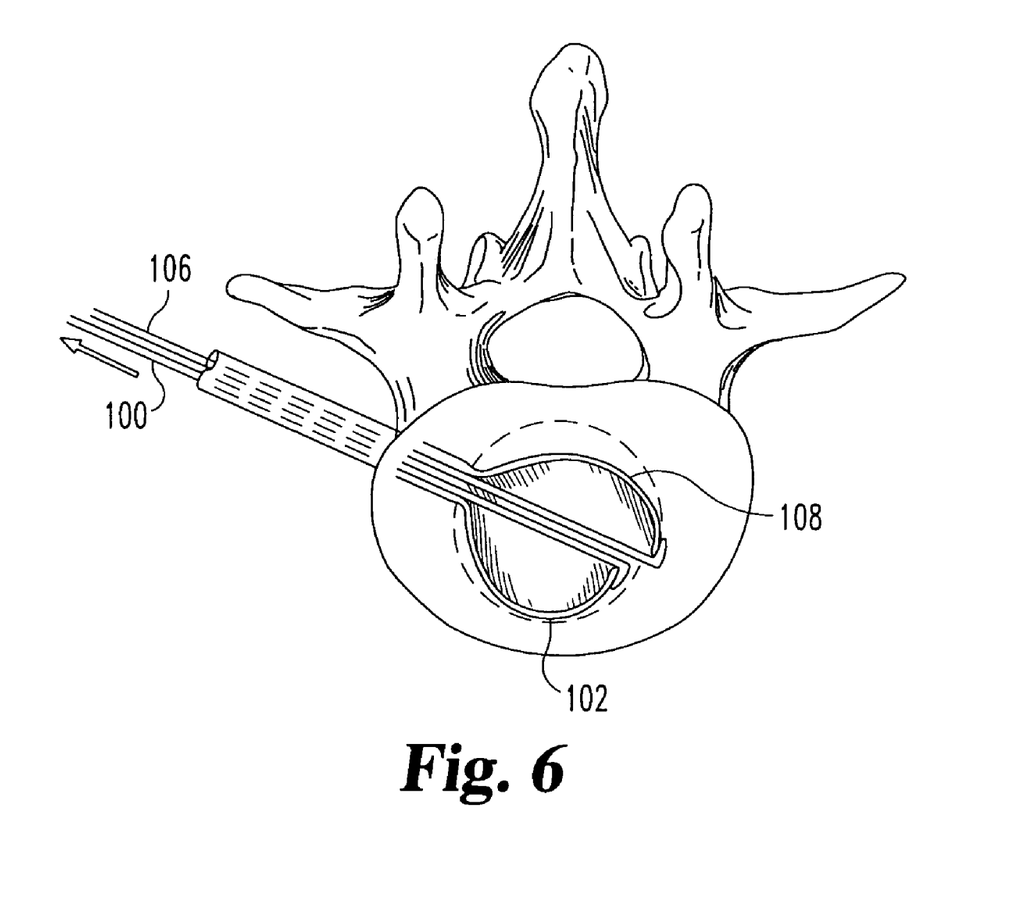
FIG. 6 is a cross section of a vertebral body illustrating a portion of a cavity creation tool.

FIG. 6 shows an embodiment of the tool that has two pull or push rods 100 and 106. Pull rod 106 operates a first arm 108 while the second arm 102 is activated by the independent pull rod 102. The asymmetrical operation of the two independent arms can be used to control the shape of the cavity by directing expansion of the cavity to preferred areas within the vertebral body.

Figure 7:
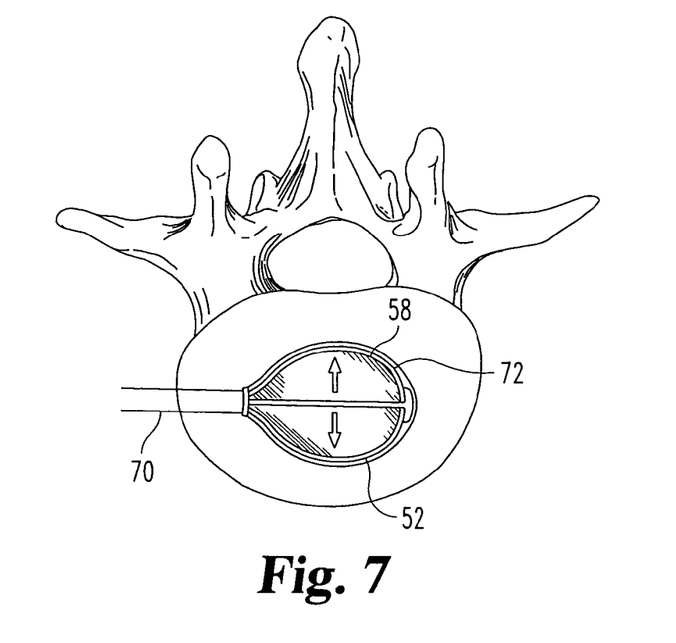
FIG. 7 is a cross section of a vertebral body illustrating a portion of a cavity creation tool.

FIG. 7 shows an embodiment of the tool 70 where a container 72 surrounds a pair of arms 52 and 58. The container interacts with the cancellous bone as the pull rod activates the arms and moves them against the cancellous bone. The container prevents debris from interfering with the retraction of the arms. The container 72 can be subsequently inflated to reduce the fracture and restore the natural anatomy. Finally, the container may be detached and left behind.

In this particular embodiment, the first and second arms are identical, and will normally create a symmetric cavity. The container 72 is optional and the arms can be used alone in a fashion analogous to other versions of the tool.

In this particular embodiment, the first and second arms have blunt dissection surfaces on the exterior of the arms to interact with cancellous bone. In this embodiment, the first and second arms may also have different mechanical properties for the creation of an asymmetric cavity.

Figure 8:
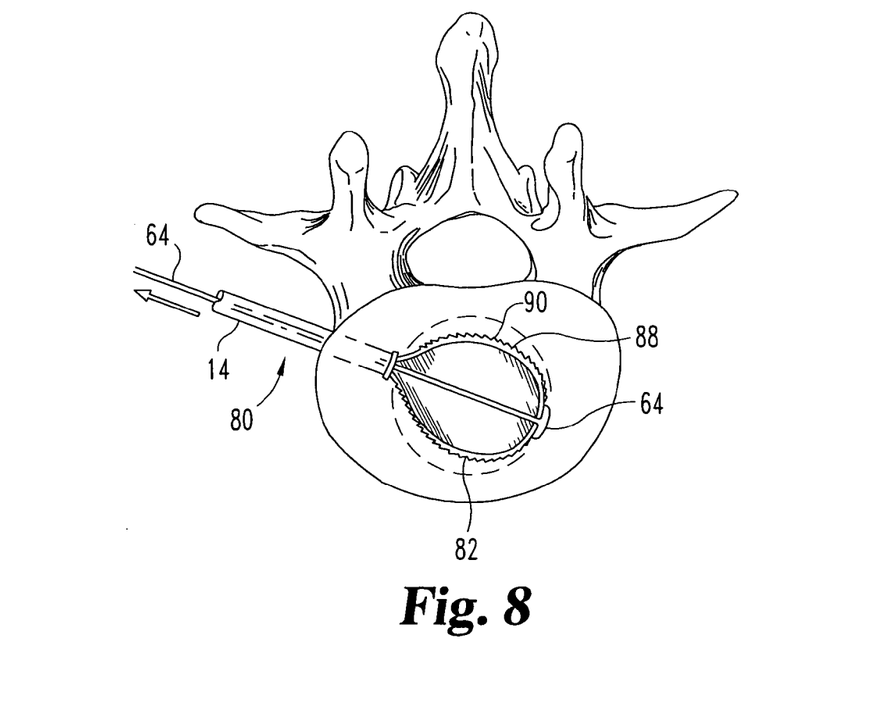
FIG. 8 is a cross section of a vertebral body illustrating a portion of a cavity creation tool.

FIG. 8 shows an embodiment of the cavity creation tool 80 that includes saw-like teeth on the first arm 88 and the second arm 82. Once again, traction on the pull rod 64 causes the teeth on the arms to cut through the cancellous bone. In a fashion similar to related embodiments, the arms lie in and define a cutting plane that creates a transverse cavity. The saw teeth typified by tooth 90 can be moved by manipulating both the pull rod and the tube.

Figure 9:
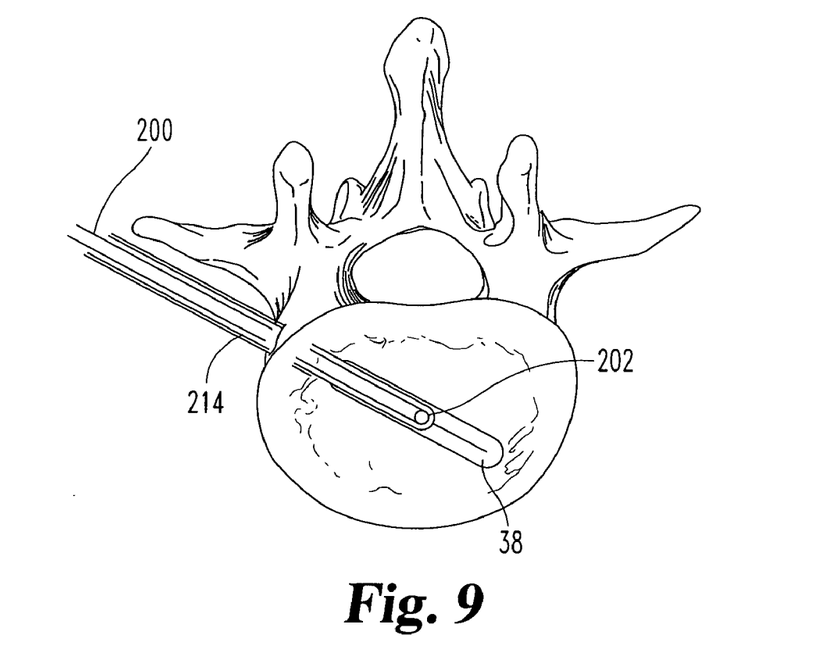
FIG. 9 is a cross section of a vertebral body illustrating a portion of a cavity creation tool.

FIG. 9 shows a cable-actuated device with a cable 200 wrapping a spindle or axle 202 mounted on the tool body 214. Cable motion results in sweeping out an arc 210 as seen in FIG. 10.

Figure 10:
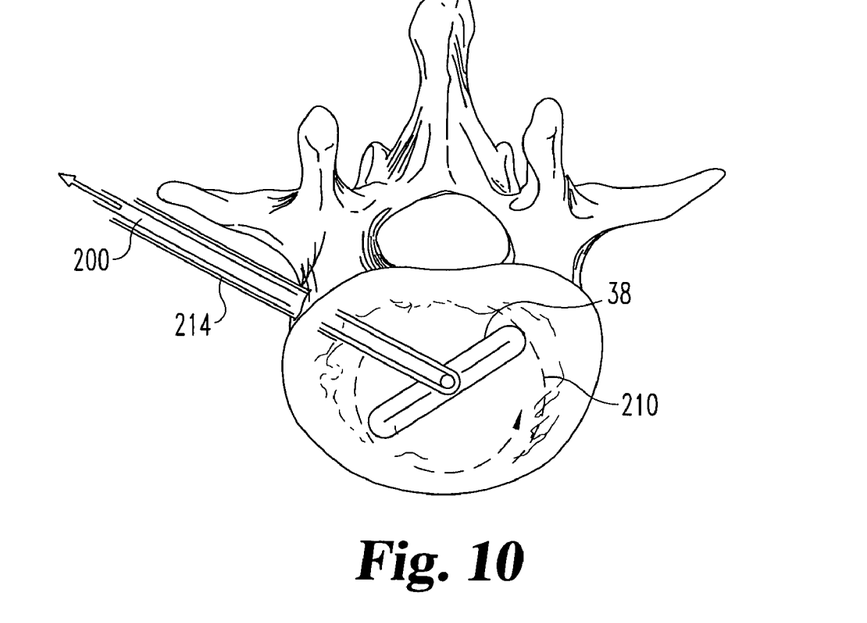
FIG. 10 is a cross section of a vertebral body illustrating a portion of a cavity creation tool.

FIG. 10 shows the blade 38 can sweep through 360 degrees because of cable actuation. An arc of less than 360 degrees may be used when a non-circular cavity is required.

Figure 11:
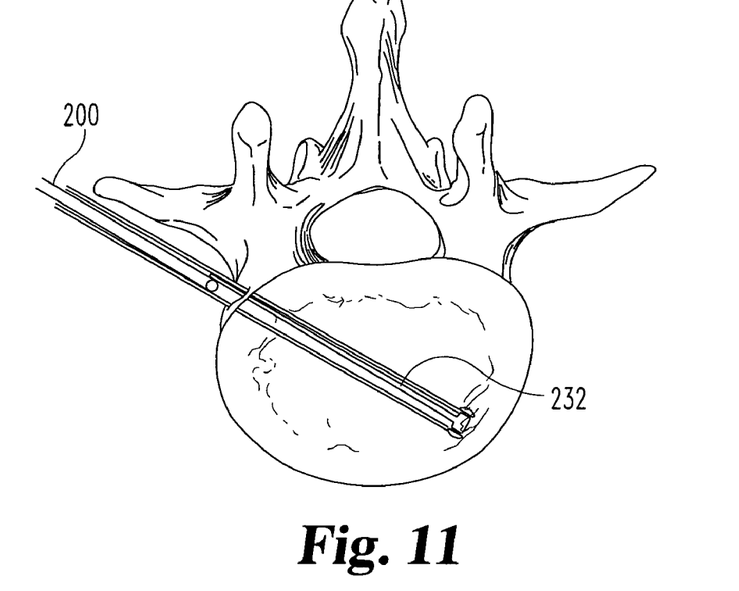
FIG. 11 is a cross section of a vertebral body illustrating a portion of a cavity creation tool.

FIG. 11 is a cable-operated version with the pull rod 232 coupled to cable 200. In this device, the pull on the cable forces the flex arms 202 and 208 in an outward direction to form the transverse cavity.

Figure 12:
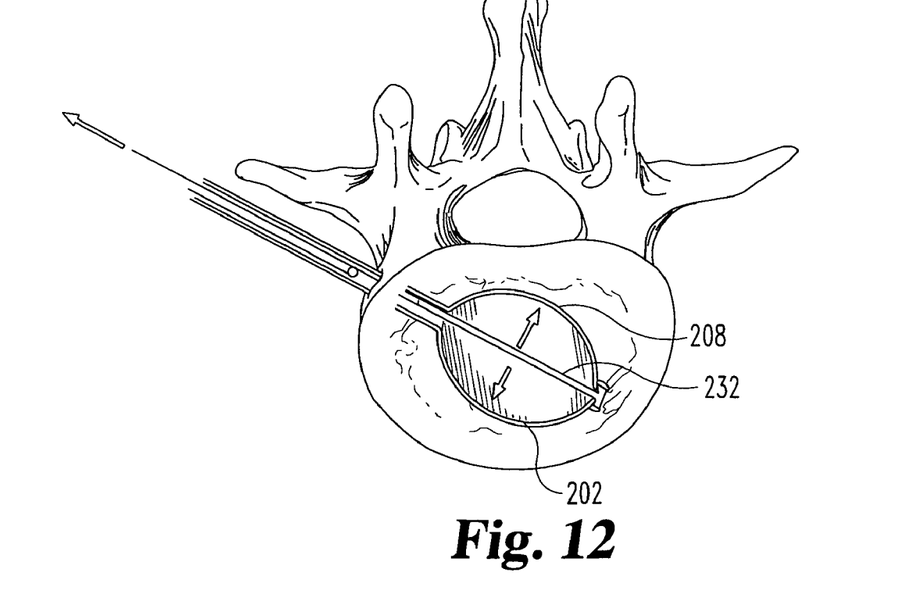
FIG. 12 is a cross section of a vertebral body illustrating a portion of a cavity creation tool.

FIG. 12 shows the cable-operated version of FIG. 9 with the arms deployed, creating a transverse cavity.

FIG. 13 which represents the prior art is a schematic of a balloon or other hydraulic lifting device as it is initially inserted into the vertebral body.

FIG. 14 is a schematic of the increased lifting force generated by a balloon or other hydraulic lifting device which immediately reaches a broad surface area because of the transverse cavity that has been prepared before deploying the balloon or hydraulic lifting device.

Although the invention has been illustrated in one context, it should be apparent that the device features maybe modified or combined in alternate configurations.

What is claimed is:

1. A method of treating a compression fracture in a bone, comprising the steps of:

forming a transverse cavity within said bone defined by at least one substantially flat surface lying substantially in a transverse plane formed by and communicating with said transverse cavity, said transverse cavity having a substantially uniform transverse extent and a maximum height, said maximum height being less than said transverse extent; and applying a force within said transverse cavity generally normal to said surface to displace said surface and restore said bone to its substantially normal anatomic position.

2. The method of claim 1, wherein said force is applied by a device expandable within said transverse cavity.

3. The method of claim 2, wherein said expandable device is configured to reach a substantially broad area of said surface upon immediate expansion and before applying said force to said surface.

4. The method of claim 3, wherein said expandable device is a hydraulic lifting device.

5. The method of claim 3, wherein said expandable device is a balloon.

6. The method of claim 2, further including the step of removing said expandable device from said transverse cavity.

7. The method of claim 2, further including the step of permanently retaining said expandable device within said transverse cavity.

8. The method of claim 2, further including the step of introducing a bone filler into said transverse cavity.

9. The method of claim 8, wherein said bone filler is introduced into said transverse cavity after applying said anatomic restoration force.

10. The method of claim 1, wherein said transverse cavity is formed by a tool inserted into said bone, said tool having a movable element capable of movement in said transverse plane, said method further including the step of activating said element to move in said transverse plane to thereby form said transverse cavity.

11. The method of claim 1, wherein the compression fractures to be treated are selected from the group consisting of vertebral compression fractures, tibial plateau fractures, distal radius fractures, calcaneous fractures, distal tibial fractures and humeral fractures.

12. A method of treating a compression fracture in a vertebral body of the spine to substantially restore normal vertebral body height, comprising the steps of:
forming within said vertebral body a transverse cavity defined by at least one substantially flat surface lying in a transverse plane extending substantially normal to the axis of the spine, said transverse cavity having a substantially uniform transverse extent and a substantially uniform height across said transverse extent, said height being less that said transverse extent;
introducing an expandable device into said transverse cavity in an unexpanded condition;
deploying said expandable device to substantially occupy said transverse cavity; and
expanding said expandable device against said surface to cause said surface to move generally along said axis of the spine to thereby restore the vertebral body height to its substantially normal anatomic height.

13. The method of claim 12, wherein said expandable device is configured to reach a substantially broad area of said surface upon immediate deployment of said device.

14. The method of claim 13, wherein said device applies a force generally normal to said surface.

15. The method of claim 14, wherein said expandable device is a hydraulic lifting device.

16. The method of claim 14, wherein said expandable device is a balloon.

17. The method of claim 12, further including the step of removing said expandable device from said transverse cavity.

18. The method of claim 12, further including the step of permanently retaining said expandable cavity within said transverse cavity.

19. The method of claim 12, further including the step of introducing a bone filler into said transverse cavity.

20. The method of claim 17, further including the step of introducing a bone filler into said transverse cavity after removing said expandable device.

21. The method of claim 12, wherein said transverse cavity is formed at a location relatively near a fracture in the vertebral body.

22. The method of claim 21, wherein said location is relatively near the anterior portion of said vertebral body.

23. The method of claim 12, wherein said transverse cavity is formed by a tool inserted into said bone, said tool having a cross-sectional area upon insertion smaller than the cross-sectional area of the transverse cavity.

24. The method of claim 23, wherein said tool has an expanse movable within said body in said transverse plane.

25. The method of claim 1, wherein said maximum height extends across said transverse extent substantially uniformly.

26. The method of claim 1, wherein the shape of said transverse cavity in the transverse plane is generally ovaloid.

* * * * *